(12) United States Patent
Ciancone et al.

(10) Patent No.: US 10,814,078 B2
(45) Date of Patent: Oct. 27, 2020

(54) INHALER SPACER AND STORAGE APPARATUS

(71) Applicant: Christopher V. Ciancone, Layton, UT (US)

(72) Inventors: Christopher V. Ciancone, Layton, UT (US); Jackson W. Murphy, Layton, UT (US)

(73) Assignee: Christopher V. Ciancone, Layton, UT (US)

( * ) Notice: Subject to any disclaimer, the term of this patent is extended or adjusted under 35 U.S.C. 154(b) by 0 days.

(21) Appl. No.: 16/409,572

(22) Filed: May 10, 2019

(65) Prior Publication Data

US 2019/0262556 A1  Aug. 29, 2019

Related U.S. Application Data

(63) Continuation of application No. 14/776,041, filed as application No. PCT/US2013/064156 on Oct. 9, 2013, now Pat. No. 10,286,162.

(Continued)

(51) Int. Cl.
*A61M 15/00* (2006.01)

(52) U.S. Cl.
CPC ...... *A61M 15/0086* (2013.01); *A61M 15/009* (2013.01); *A61M 15/0021* (2014.02); *A61M 2205/3584* (2013.01)

(58) Field of Classification Search
CPC ............ A61M 15/0086; A61M 15/009; A61M 15/0021; A61M 2205/3584
See application file for complete search history.

(56) References Cited

U.S. PATENT DOCUMENTS 3,184,115 A   5/1965  Meshberg
3,994,421 A   11/1976 Hanson
(Continued)

FOREIGN PATENT DOCUMENTS

AU   1999026689 A1   11/1999
AU      749087 B2    6/2002
(Continued)

OTHER PUBLICATIONS

U.S. Appl. No. 14/776,041, Notice of Allowance, dated Jan. 3, 2019, 5 pages.
(Continued)

*Primary Examiner* — Steven O Douglas
(74) *Attorney, Agent, or Firm* — Stoel Rives LLP

(57) ABSTRACT

A spacer may improve the effectiveness of medication delivery by an inhaler. The spacer may be configured to store the inhaler to improve compactness and/or portability of the spacer and inhaler. The inhaler may be coupled to a retaining device, inhaler container, and/or the like that restricts movement of the inhaler to predetermined positions and/or orientations. A user may be able to transition the inhaler between a stored position and an active position by moving the inhaler translationally and/or rotationally. The inhaler may be able to remain coupled to the retaining device and/or inhaler container, and the retaining device and/or inhaler container may be able to remain coupled to the spacer during transition from the stored position to the active position. The spacer may be sized to fit in a pants pocket in an embodiment.

21 Claims, 14 Drawing Sheets

Related U.S. Application Data

(60) Provisional application No. 61/798,817, filed on Mar. 15, 2013, provisional application No. 61/798,488, filed on Mar. 15, 2013.

(56) References Cited

U.S. PATENT DOCUMENTS

| | | | |
|---|---|---|---|
| 4,509,515 | A | 4/1985 | Altounyan et al. |
| 4,796,614 | A | 1/1989 | Nowacki et al. |
| 4,852,561 | A | 8/1989 | Sperry |
| 5,284,133 | A * | 2/1994 | Burns ............... A61M 15/009 128/200.14 |
| 5,505,194 | A * | 4/1996 | Adjei ............... A61M 15/0086 128/200.23 |
| 5,724,986 | A | 3/1998 | Jones et al. |
| 5,775,320 | A | 7/1998 | Patton et al. |
| 5,809,997 | A * | 9/1998 | Wolf ................ A61M 15/009 128/200.23 |
| 5,839,429 | A * | 11/1998 | Marnfeldt ........... A61M 15/00 128/200.14 |
| 5,904,139 | A | 5/1999 | Hauser |
| 6,286,506 | B1 | 9/2001 | McAndrew et al. |
| 6,397,840 | B1 | 6/2002 | Chrai et al. |
| 6,418,925 | B1 | 7/2002 | Genova et al. |
| 6,595,204 | B2 | 7/2003 | Genova et al. |
| 6,595,206 | B2 | 7/2003 | Vito |
| 6,684,880 | B2 * | 2/2004 | Trueba .............. A61M 15/0085 128/200.16 |
| 6,698,422 | B2 | 3/2004 | Fugelsang et al. |
| 6,752,148 | B1 | 6/2004 | McGinn et al. |
| 6,792,941 | B2 | 9/2004 | Andersson |
| 6,932,082 | B2 | 8/2005 | Stein |
| 7,107,987 | B2 * | 9/2006 | Sundaram ......... A61M 15/0086 128/200.22 |
| 7,178,518 | B2 | 2/2007 | Watt et al. |
| 7,198,044 | B2 | 4/2007 | Trueba |
| 7,225,807 | B2 | 6/2007 | Papania et al. |
| 7,284,553 | B2 | 10/2007 | Hochrainer |
| 7,343,914 | B2 | 3/2008 | Abrams et al. |
| 7,360,537 | B2 | 4/2008 | Snyder et al. |
| 7,556,037 | B2 | 7/2009 | Klein |
| 7,624,731 | B2 | 12/2009 | Walstrom |
| 7,832,393 | B2 | 11/2010 | Vito |
| 7,861,713 | B2 | 1/2011 | Dhuper et al. |
| 7,878,193 | B2 | 2/2011 | Kladders et al. |
| 7,891,358 | B2 | 2/2011 | Kolb et al. |
| 7,950,389 | B2 | 5/2011 | Eason et al. |
| 7,980,491 | B2 | 7/2011 | Kakade et al. |
| 7,984,713 | B2 | 7/2011 | Hochrainer et al. |
| 8,001,965 | B2 | 8/2011 | Kladders et al. |
| 10,286,162 | B2 * | 5/2019 | Ciancone .......... A61M 15/0086 |
| 2002/0073992 | A1 | 6/2002 | Andersson et al. |
| 2002/0121276 | A1 | 9/2002 | Genova et al. |
| 2002/0157664 | A1 | 10/2002 | Fugelsang et al. |
| 2006/0000471 | A1 | 1/2006 | Klein |
| 2006/0130838 | A1 | 6/2006 | Lee et al. |
| 2006/0219243 | A1 | 10/2006 | Walstrom |
| 2007/0006883 | A1 | 1/2007 | Kolb et al. |
| 2007/0074718 | A1 | 4/2007 | Austin |
| 2008/0087279 | A1 | 4/2008 | Tieck et al. |
| 2008/0115785 | A1 | 5/2008 | Eason et al. |
| 2008/0178872 | A1 * | 7/2008 | Genova ............. A61M 15/0065 128/200.23 |
| 2008/0210225 | A1 | 9/2008 | Geiger |
| 2008/0251551 | A1 | 10/2008 | Huber et al. |
| 2008/0257345 | A1 | 10/2008 | Snyder et al. |
| 2009/0024112 | A1 * | 1/2009 | Edwards ............... A61M 5/19 604/890.1 |
| 2009/0032019 | A1 | 2/2009 | Green et al. |
| 2009/0064996 | A1 | 3/2009 | Rosh |
| 2009/0301472 | A1 | 12/2009 | Kim et al. |
| 2010/0163045 | A1 | 7/2010 | Powell et al. |
| 2010/0212665 | A1 | 8/2010 | Zhao |
| 2010/0258118 | A1 | 10/2010 | Morton |
| 2011/0240015 | A1 | 10/2011 | Nikander et al. |
| 2011/0277760 | A1 | 11/2011 | Terry et al. |
| 2012/0240922 | A1 | 9/2012 | Denyer et al. |
| 2015/0273165 | A1 * | 10/2015 | Hadash ............. A61M 15/0065 128/203.14 |

FOREIGN PATENT DOCUMENTS

| | | |
|---|---|---|
| AU | 755755 B2 | 12/2002 |
| EP | 0235333 B1 | 5/1989 |
| EP | 0683890 A1 | 11/1995 |
| EP | 1126891 B1 | 12/2003 |
| EP | 1059951 B1 | 1/2005 |
| EP | 1292395 B1 | 1/2008 |
| EP | 1684834 B1 | 7/2011 |
| EP | 2381991 B1 | 7/2012 |
| WO | 1987006475 A1 | 11/1987 |
| WO | 1999044663 A1 | 9/1999 |
| WO | 2000027456 A1 | 5/2000 |
| WO | 2004060260 A2 | 7/2004 |
| WO | 2008053253 A2 | 5/2008 |
| WO | 2011067692 A1 | 6/2011 |
| WO | 2011130583 A2 | 10/2011 |
| WO | 2012026963 A2 | 3/2012 |
| WO | 2012114322 A1 | 8/2012 |

OTHER PUBLICATIONS

U.S. Appl. No. 14/776,041, Non-Final Office Action, dated Jun. 20, 2018, 8 pages.
U.S. Appl. No. 14/776,041, Non-Final Office Action, dated Nov. 22, 2017, 6 pages.
Battistini, "The best way to use aerosolic treatment. Part 1—Methods", Ped. Med. Chir. (Med. Surg. Pef.), 17.2, Mar.-Apr. 1995, pp. 97-103.
Boulet, et al., "Update on inhalation therapy in asthma and obstructive bronchopulmonary diseases", L'Union Medicale Du Canada 123.1, Jan. 1994, pp. 23-31.
Brambilla, "Plume temperature emitted from metered dose inhalers", International Journal of Pharmaceutics 405, 2011, pp. 9-15.
Brocklebank, et al., "Comparison of the effectiveness of inhaler devices in asthma and chronic obstructive airways disease: a systematic review of the literature", Health Technology Assessment; vol. 5; No. 26, 2001, 155 pages.
Clancy, "Cross-infection and the use and decontamination of placebo inhalers", British Journal of Nursing, vol. 12, No. 13, Jul. 2003, pp. 778-783.
Dalby, et al., "Evaluation of Aersol Drug Output from the OptiChamber and AeroChamber Spacers in a Model System", Journal of Asthma, 35(2), 1998, pp. 173-177.
Dempsey, et al., "Evaluation of the Effect of a Large Volume Spacer on the Systemic Bioactivity of Fluticasone Propionate Metered-Dose Inhaler", CHEST Journal 116.4, Oct. 1999, pp. 935-940.
Devadason, "Recent Advances in Aerosol Therapy for Children with Asthma", Journal of Aerosol Medicine, vol. 19, No. 1, 2006, pp. 61-66.
Dewar, et al., "A randomised controlled trial to assess the relative benefits of large volume spacers and nebulisers to treat acute asthma in hospital", Arch Dis Child vol. 80, May 1999, pp. 421-423.
Dubus, et al., "Emitted doses of salbutamol pressurized metered-dose inhaler from five different plastic spacer devices", Fundam. Clin. Pharmacol. vol. 14, May-Jun. 2000, pp. 219-224.
Lipworth, et al., "Lung delivery of non-CFC salbutamol via small volume metal spacer and large volume plastic spacer devices compared with an open vent jet nebulizer", Br. J. Clin. Pharmacol. vol. 45, Feb. 1998, pp. 160-163.
Nakhla, "A homemade modification of a spacer device for delivery of bronchodilator or steroid therapy in patients with tracheostomies", The Journal of Laryngology and Otology, vol. III, Apr. 1997, pp. 363-365.
Newman, et al., "Comparison of Beclomesthasone Dipropionate Delivery by Easyhaler Dry Powder Inhaler and pMDI Plus Large Volume Spacer", Journal of Aerosol Medicine, vol. 14, No. 2, 2001, pp. 217-225.

(56) References Cited

OTHER PUBLICATIONS

Newman, "Spacer Devices for Metered Does Inhalers", Clin. Pharmacokinetics, vol. 43.6, 2004, pp. 349-360.
PCT/US2013/064156, International Search Report and Written Opinion, dated Jan. 8, 2014, 13 pages.
Sharma, "Plenary Lecture : Inhaled Drug Delivery, Past, Present and Future: A Therapeutic Perspective", Journal of Aerosol Medicine 13.1, 2000, pp. 59-72.
Silkstone, et al., "Relative lung and total systemic bioavailability following inhalation from a metered dose inhaler compared with a metered dose inhaler attached to a large volume plastic spacer and a jet nubuliser", European Respiratory Journal Pharmacology 57.11, Jan. 2002, pp. 781-786.
Thorsson, et al., "Lung deposition of budesonide from a pressurized metered-dose inhaler attached to a spacer", Eur. Respir. J. 12.6, 1998, pp. 1340-1345.
Tuley, "Experimental Dry Powder Inhaler Flow Visulalization—A Proof of Concept", May 2003, 72 pages.
Wildhaber, et al., "Electrostatic charge on a plastic spacer device influences the delivery of salbutamol", European Respiratory Journal 9.9, 1996, pp. 1943-1946.

\* cited by examiner

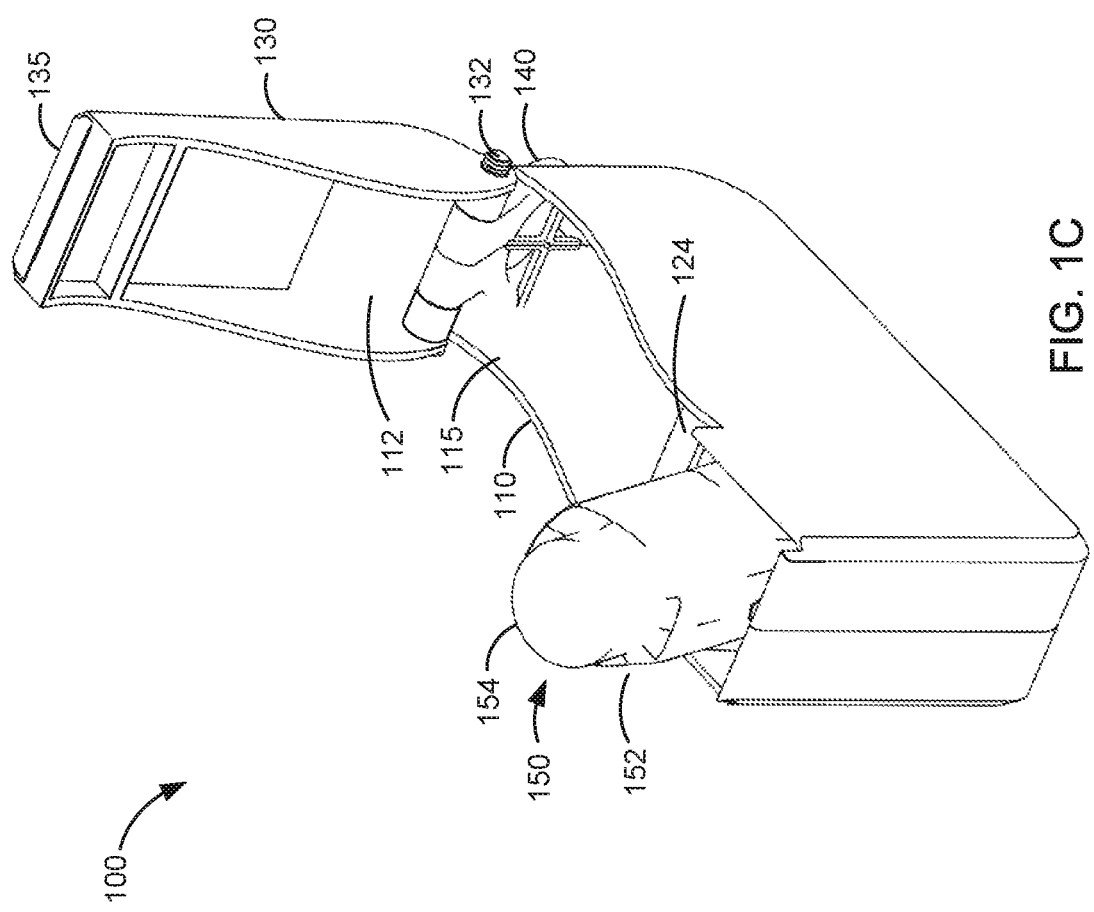

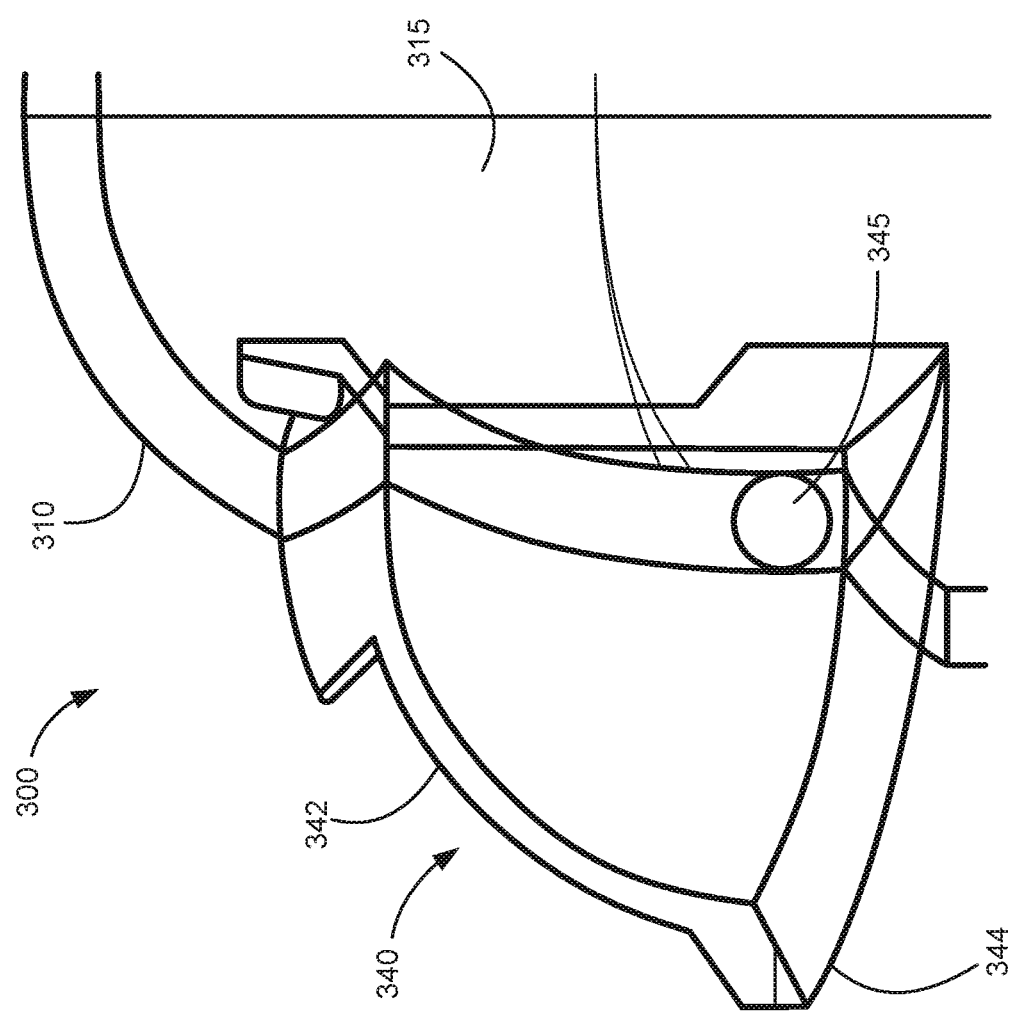

> US 10,814,078 B2

INHALER SPACER AND STORAGE APPARATUS

RELATED APPLICATIONS

This application is a continuation of U.S. Patent Application with application Ser. No. 14/776,041 filed on Sep. 14, 2015, which is the National Stage of International Application No. PCT/US2013/064156 filed on Oct. 9, 2013, which claims priority to U.S. Provisional Patent Application with Ser. No. 61/798,488 filed on Mar. 15, 2013 and entitled "Inhaler Device (Slyder)" and U.S. Provisional Patent Application with Ser. No. 61/798,817 filed on Mar. 15, 2013 and entitled "Inhaler Device (1-Piece)." Each one of the aforementioned applications is hereby incorporated by reference herein in their entirety.

TECHNICAL FIELD

This disclosure relates to an inhaler spacer that is able to store an inhaler.

BRIEF DESCRIPTION OF THE DRAWINGS

FIG. 1C is a rear perspective view of the spacer shown in FIG. 1A with the inhaler in the active position and the cover open.

FIG. 3C is a cross-section view of the concealable mouthpiece shown in FIG. 3A in an active position.

DETAILED DESCRIPTION OF PREFERRED EMBODIMENTS

Figure 1A:
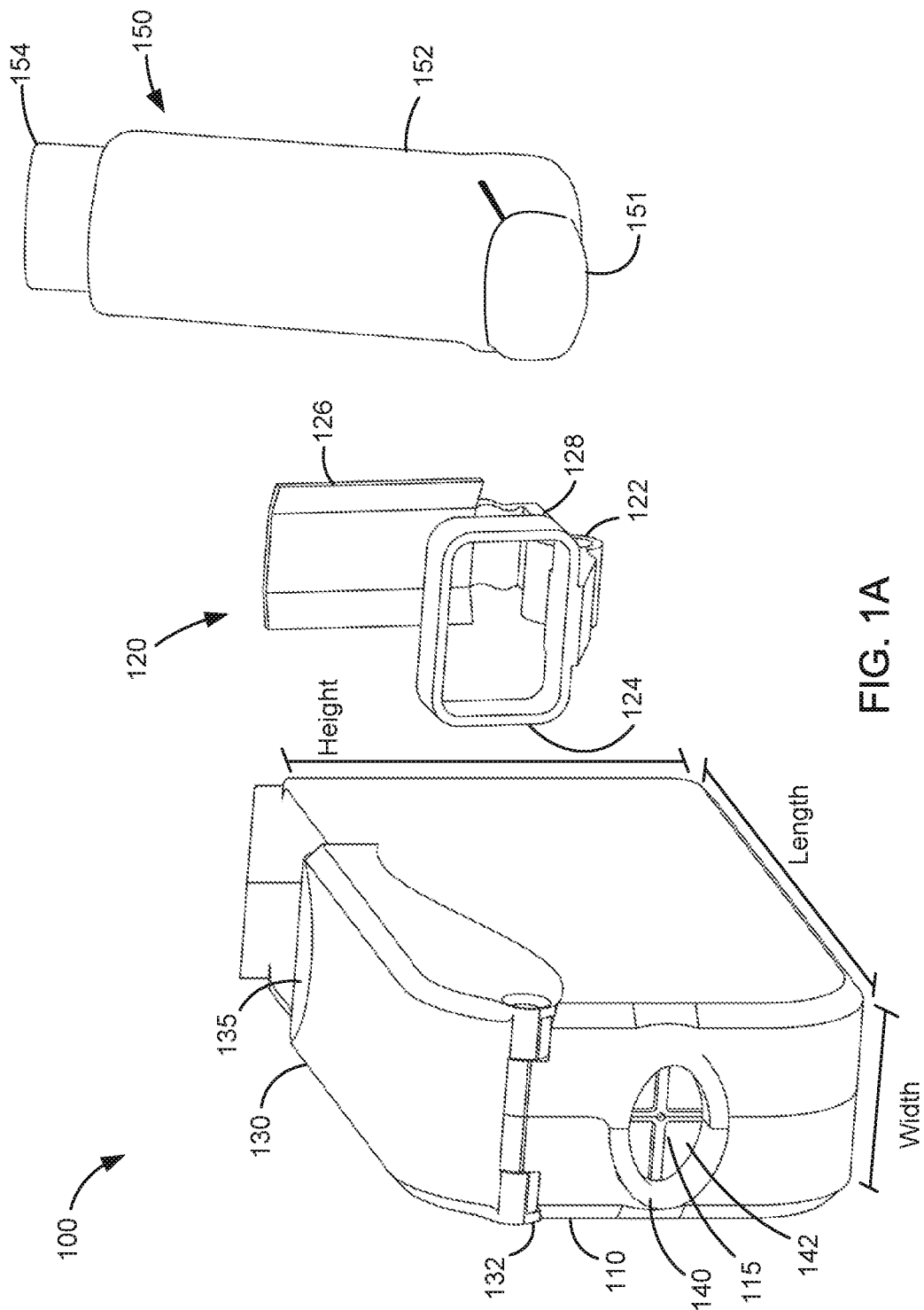
FIG. 1A is a disassembled perspective view of a spacer, a retaining device, and an inhaler according to one embodiment.

Asthma, chronic obstructive pulmonary disease (COPD) and other respiratory diseases negatively impact the lives of millions of people. Inhalers, such as pressurized metered-dose inhalers (pMDIs), propellant-free soft mist inhalers (SMIs), and the like, may be used to direct medication to a person's airway in order to manage and/or treat diseases, such as asthma and COPD. When used alone, these inhalers are very inefficient and may provide an average deposition of medication to the lower airway target as low as 20% or less.

Deposition in the lower airway target may be improved by using a spacer. While a spacer may markedly increase lung and/or lower airway drug deposition, it may suffer the shortcoming of being too large and bulky for practical daily use outside the home. Furthermore, conventional spacers fail to integrate the spacer and inhaler for improved storage and use. Therefore, there is a need for a spacer that is both extremely portable and easy to use. The number of patients who self-administer inhalable drugs is set to increase significantly in the coming years as many medications, such as insulin for diabetics and cancer therapy drugs, are being developed in an inhalable form. Accordingly, a device that will garner high patient compliance is critically needed.

FIGS. 1A-1E are perspective and cross-section views of an embodiment of a spacer 100 configured to store an inhaler 150. The spacer 100 may include a spacer housing 110 that defines a spacer chamber 115. The spacer chamber 115 may receive medication discharged by the inhaler 150 and may slow the delivery of the medication so more of the medication can reach the lower airway of the user when the user inhales. The spacer chamber 115 may slow the delivery of the medication by providing additional distance between the inhaler and the user's mouth, which may allow air friction to slow the velocity of the medication. The spacer housing 110 may constrain the medication from dispersing and hold the medication until it can be inhaled by the user.

The spacer chamber 115 may be elongated along a longitudinal axis. The medication may be discharged substantially along the elongated longitudinal axis, and the medication may have space to slow before impacting the spacer housing 110. The length of the spacer housing 110 along the longitudinal axis may be selected to be short enough for the spacer 100 to fit in a pants pocket (e.g., the length may be selected to be less than or equal to the length of a selected pants pocket and/or to completely conceal the spacer in the selected pants pocket) but long enough to slow medication without substantial deposition of the medication on the spacer housing.

A cross-section of the spacer chamber 115 normal to the longitudinal axis may be any of various shapes, such as a circle, an oval, a square with or without rounded corners, a rectangle with or without rounded corners, a hybrid between shapes, etc., and/or the size and/or shape of the cross-section may vary at different points along the longitudinal axis. In the illustrated embodiment, the spacer housing 110 forms a rectangular prism with rounded edges, which has a rectangular cross-section with rounded corners. In some embodiments, a height of the cross-section along a vertical axis may be larger than a width along a lateral axis. The additional height may provide space for manipulating the inhaler 150, as discussed in further detail below. The height of the cross-section may be selected to be short enough for the spacer 100 to fit in a pants pocket (e.g., the height of the cross-section may be selected to be less than the width of a selected pants pocket) but tall enough to permit manipulation of the inhaler 150. The width of the cross-section may be selected to be wide enough for an inhaler 150 to fit in the spacer chamber 115 (e.g., the width of the cross-section may be greater than or equal to the width of the inhaler 150) but otherwise may be selected to be as narrow as possible (e.g., as close to the width of the inhaler 150 as possible without restricting manipulation). The width may affect what height can fit in a pants pocket, so the width plus height may be selected to be less than the width of the selected pants pocket.

The spacer housing 110 may include a concave wall 112 configured to reflect medication received from the inhaler 150 back into the spacer chamber 115. More medication may be deposited on corners, edges, flat surfaces, and the like than concave surfaces, which may direct the medication back into the spacer chamber 115 with minimal deposition. The concave wall 112 may be located at an edge opposite the inhaler 150, which may maximize the distance between the inhaler 150 and the concave wall 112. The inhaler 150 may be slightly angled relative to the longitudinal axis to aim at the concave wall 112. The concave wall 112 and/or the spacer housing 110 may be made of a material selected to minimize deposition of the medication, such as a non-adhesive material (e.g., polytetrafluoroethylene). Alternatively, or in addition, the spacer housing 110 may be made of a light-weight material that is resistant to deformation, such as aluminum, anti-static coated aluminum, a polymer (e.g., polycarbonate), carbon fiber, carbon-fiber-reinforced polymer, and/or the like.

The spacer 100 may include a retaining device 120 configured to receive the inhaler 150. The retaining device 120 may restrict movement of the inhaler 150 and may allow the inhaler 150 to be manipulated into predetermined positions and/or orientations. For example, in the illustrated embodiment, the retaining device 120 may include a ring 122 configured to rotatably couple with a rod 121 protruding from and/or coupled to the spacer housing 110. The rod 121 may define a coincident pivot point about which the retaining device 120 rotates. In alternate embodiments, the retaining device 120 may include a rod (not shown) and the spacer housing 110 may include a cavity (not shown) that allows the rod to rotate and/or move translationally. The retaining device 120 may include a restraining band 124 configured to encircle an inhaler mouthpiece 151 on the inhaler 150. In an embodiment, the restraining band 124 may include one or more stiff wires encircling the inhaler 150. The retaining device 120 may also include a backing 126 and a base 128. The restraining band 124, backing 126, and base 128 may hold the inhaler 150 sufficiently snugly to prevent excessive movement and/or inadvertent dislodgement by the inhaler but loose enough for the inhaler 150 to be inserted and removed from the retaining device 120 by the user.

Figure 1B:
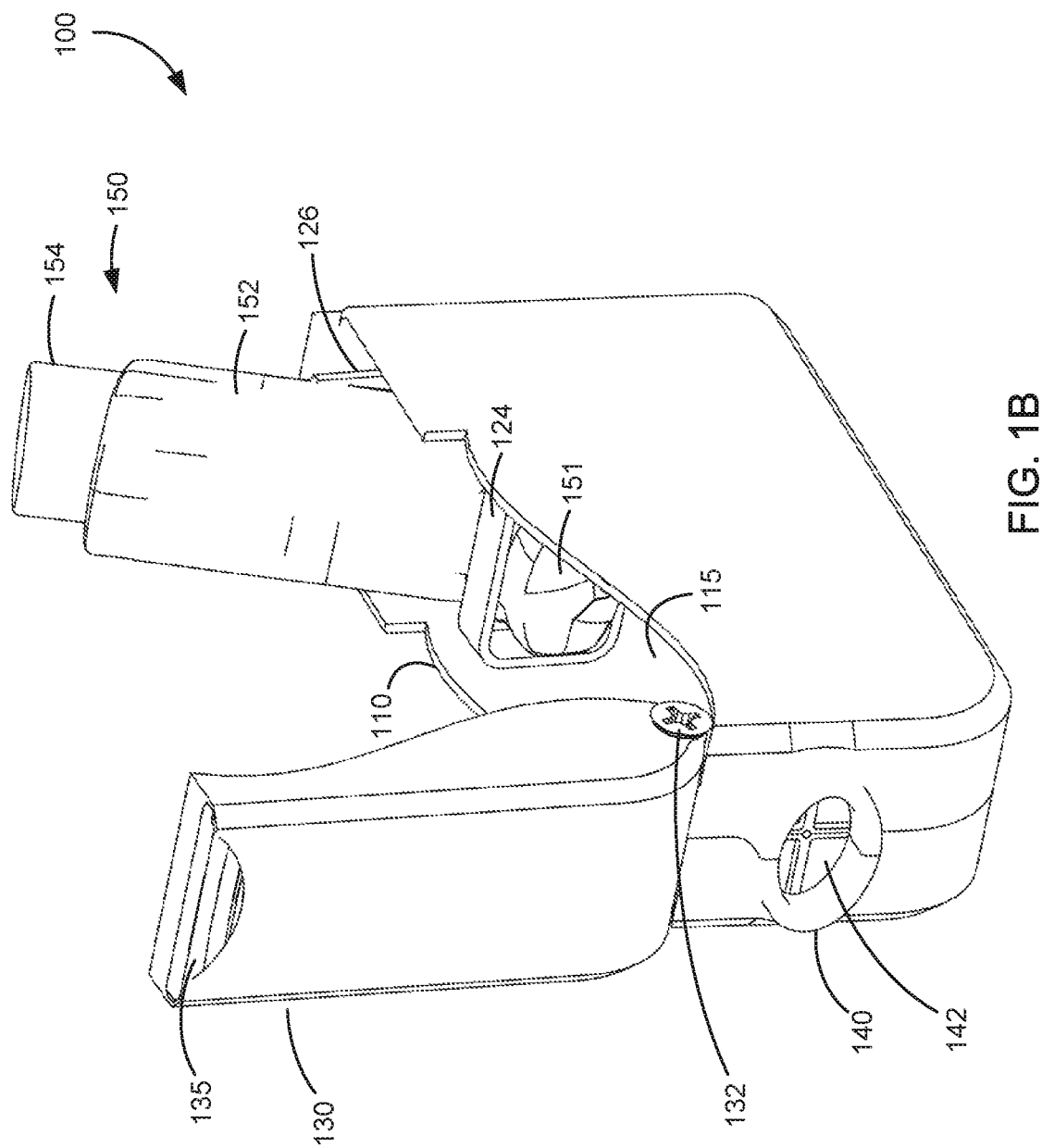
FIG. 1B is a front perspective view of the spacer shown in FIG. 1A with the inhaler in an active position and a cover open.
Figure 1D:
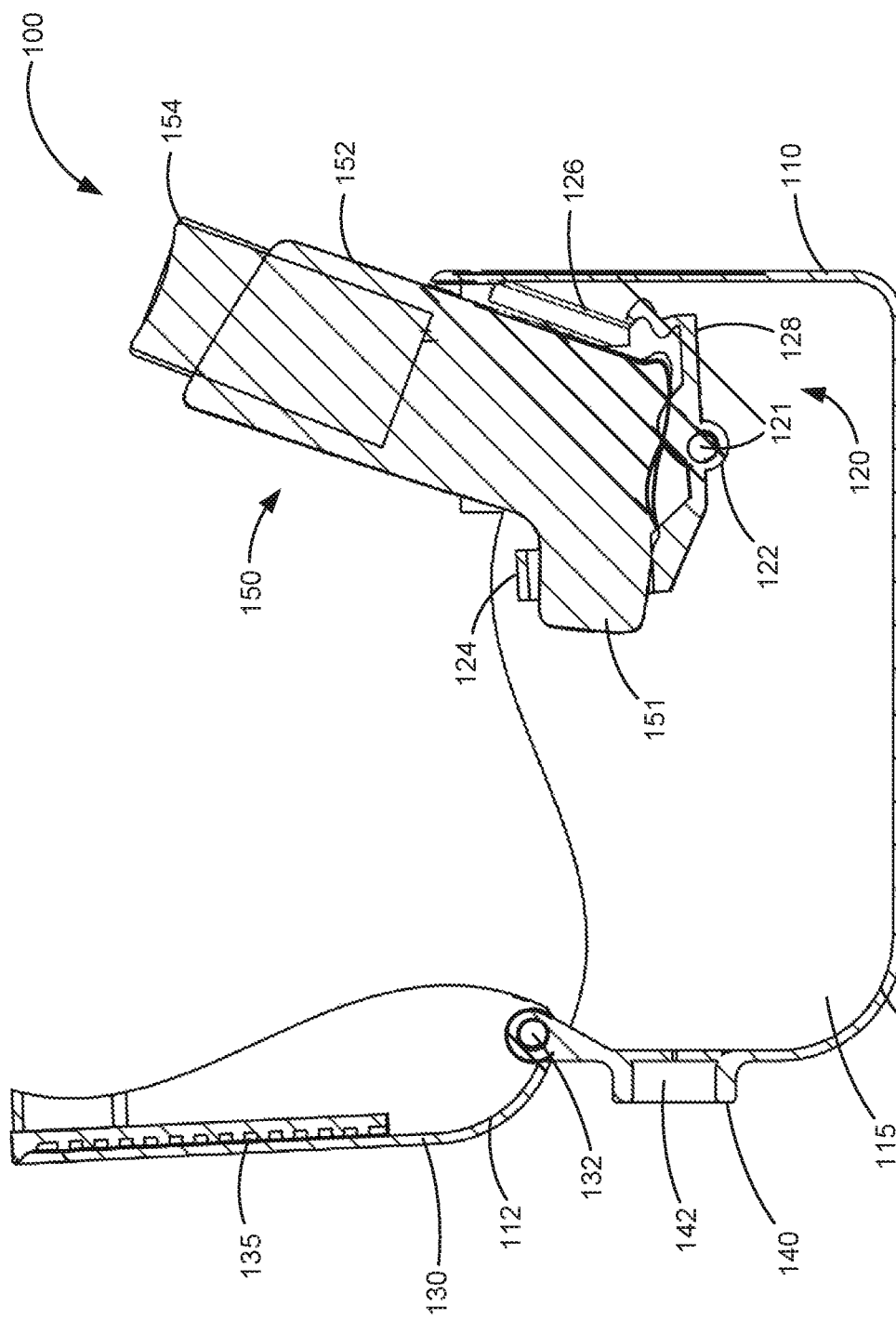
FIG. 1D is a cross-section view of the spacer shown in FIG. 1A with the inhaler in the active position and the cover open.
Figure 1E:
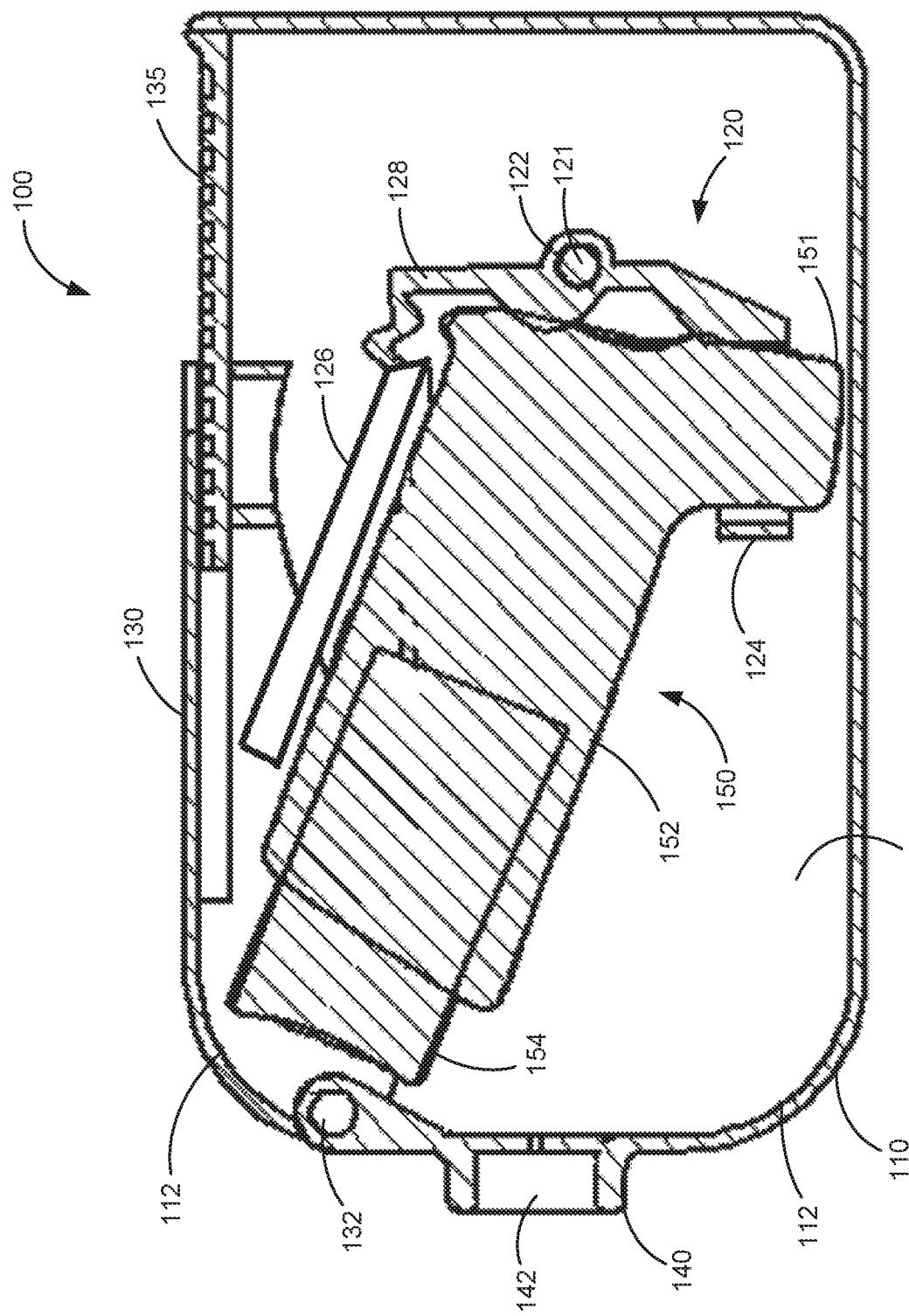
FIG. 1E is a cross-section view of the spacer shown in FIG. 1A with the inhaler in a stored position, the cover closed, and a sliding door fully extended.
Figure 2A:
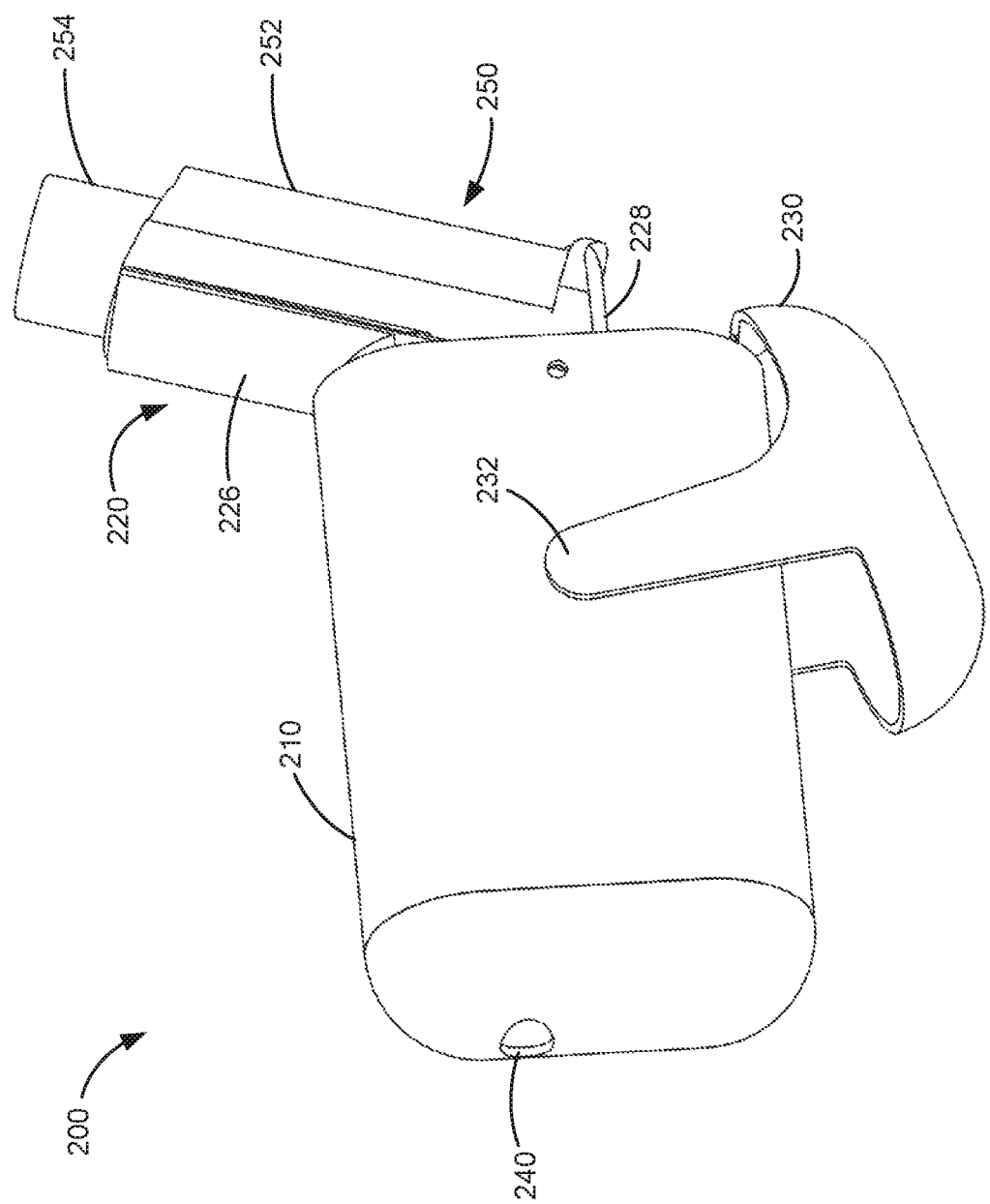
FIG. 2A is a front perspective view of a spacer with an inhaler in an active position and a cover open according to another embodiment.
Figure 2B:
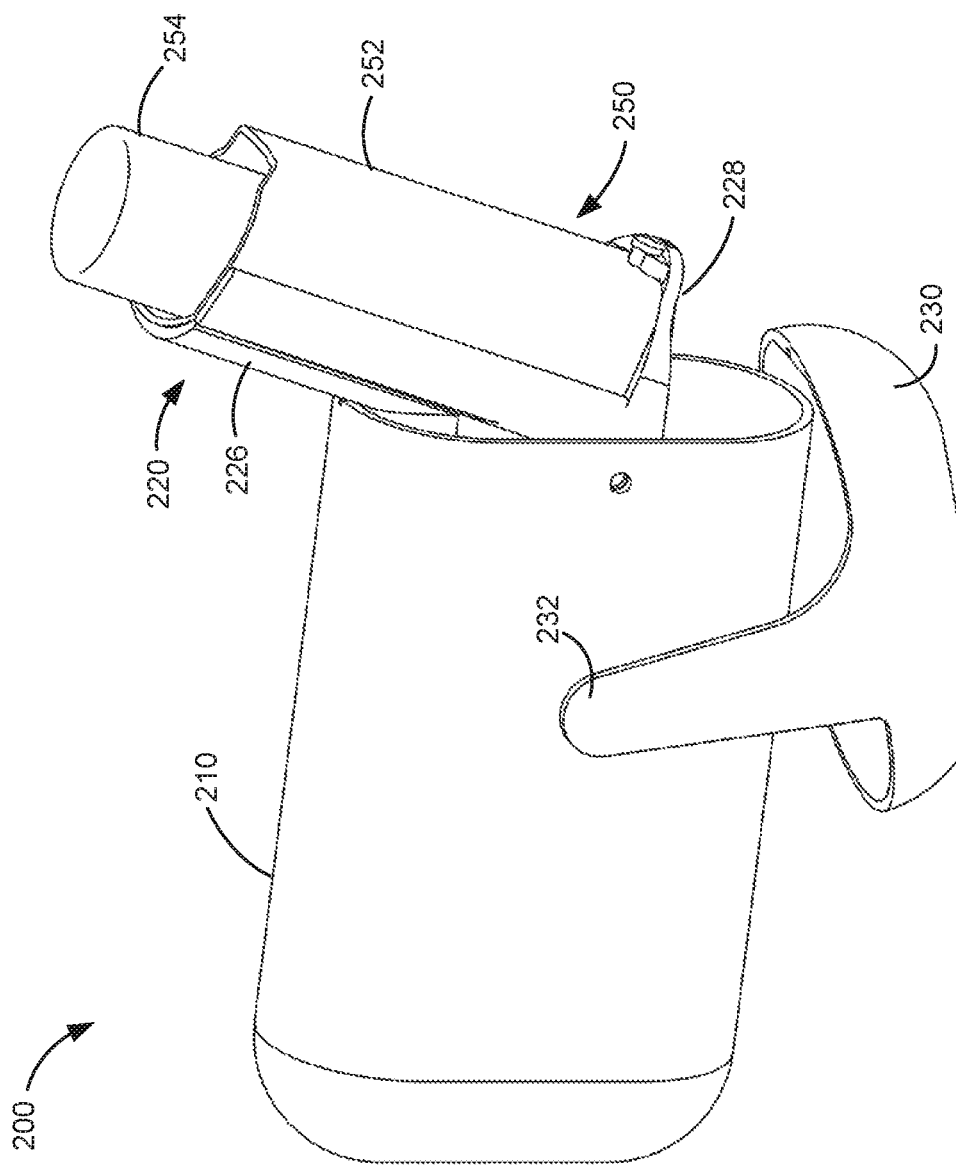
FIG. 2B is a rear perspective view of the spacer shown in FIG. 2A with the inhaler in the active position and the cover open.
Figure 2C:
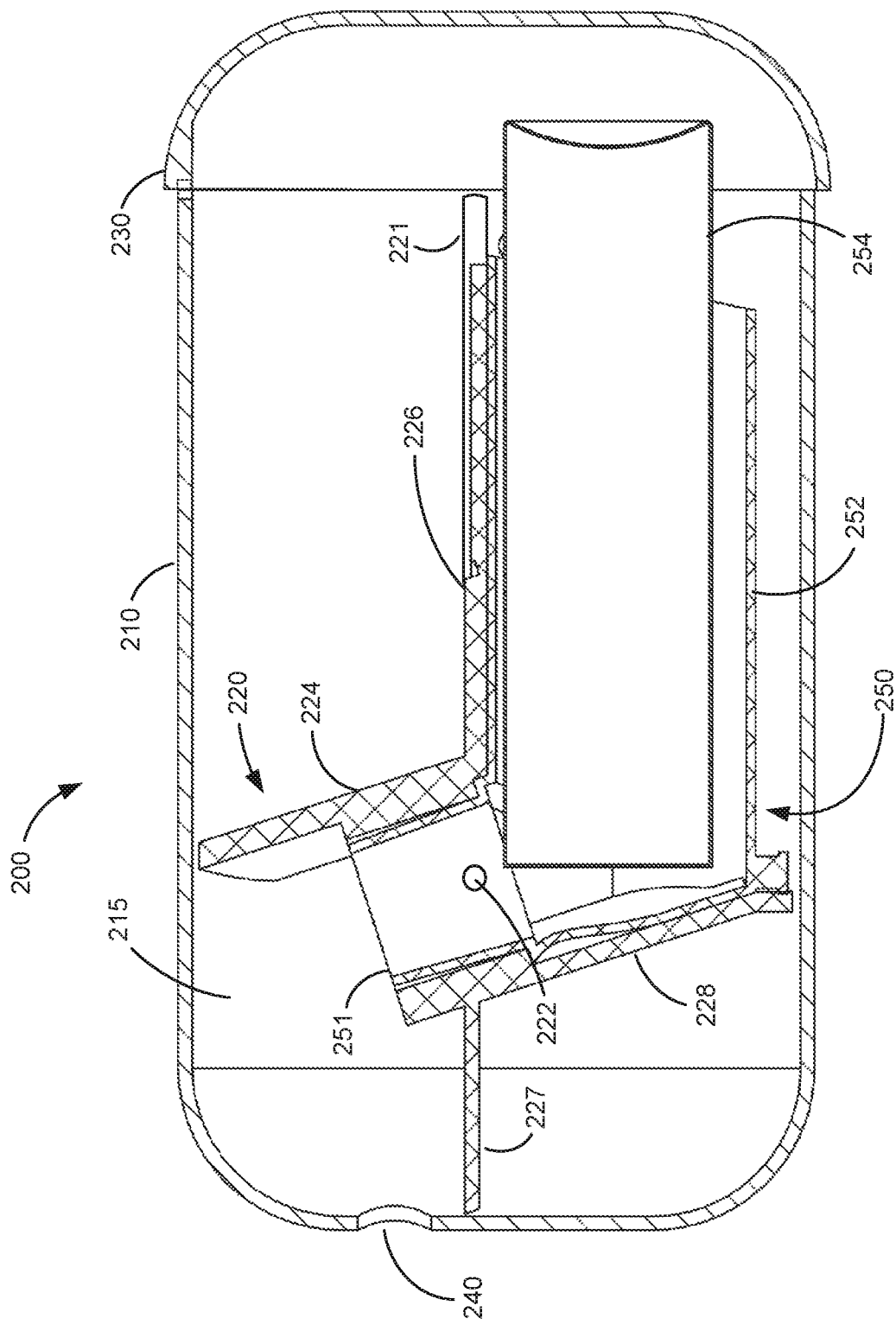
FIG. 2C is a cross-section view of the spacer shown in FIG. 2A with the inhaler in a stored position and the cover closed.
Figure 2D:
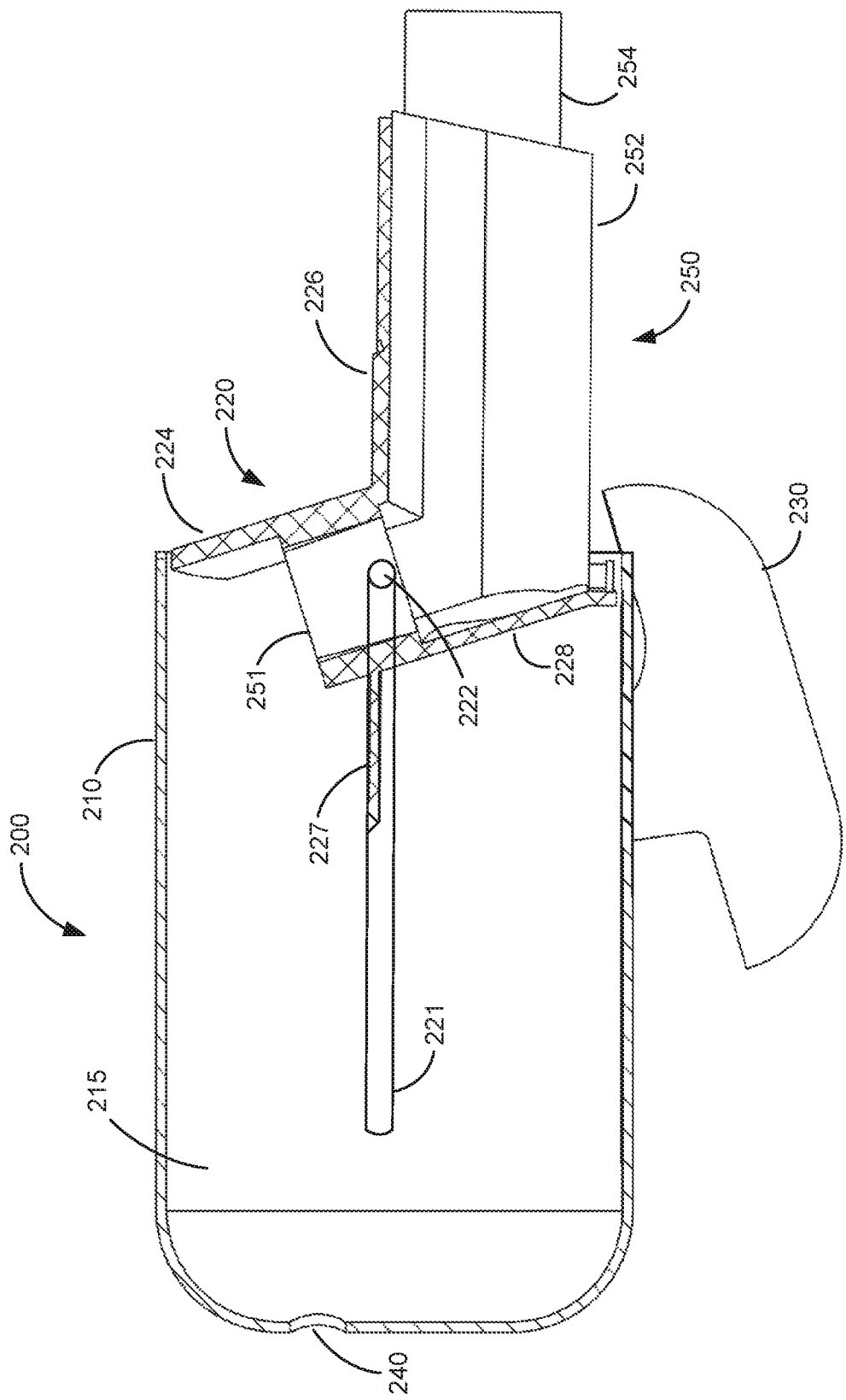
FIG. 2D is a cross-section view of the spacer shown in FIG. 2A with the inhaler being transferred from the stored position to the active position and the cover open.
Figure 2E:
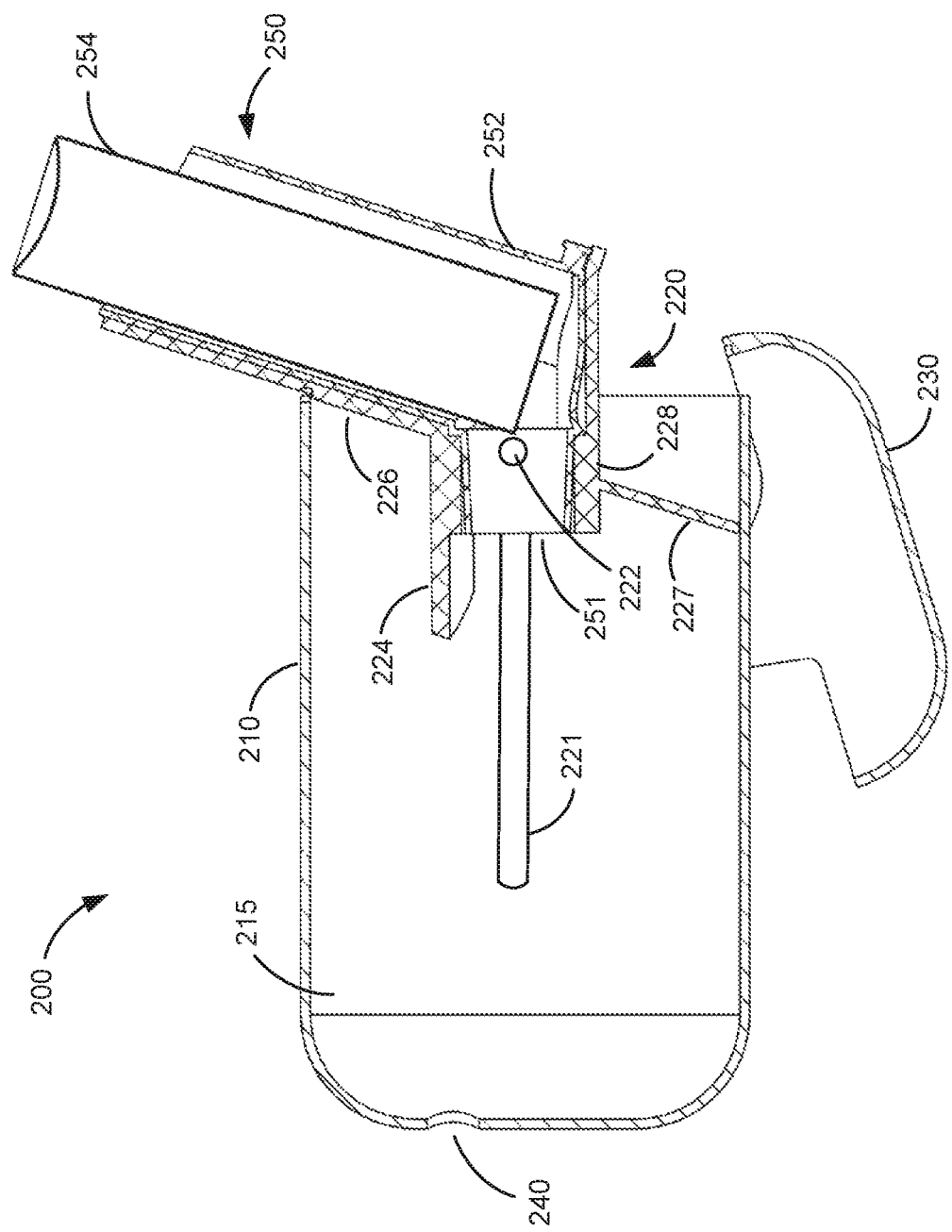
FIG. 2E is a cross-section view of the spacer shown in FIG. 2A with the inhaler in the active position and the cover open.
Figure 3A:
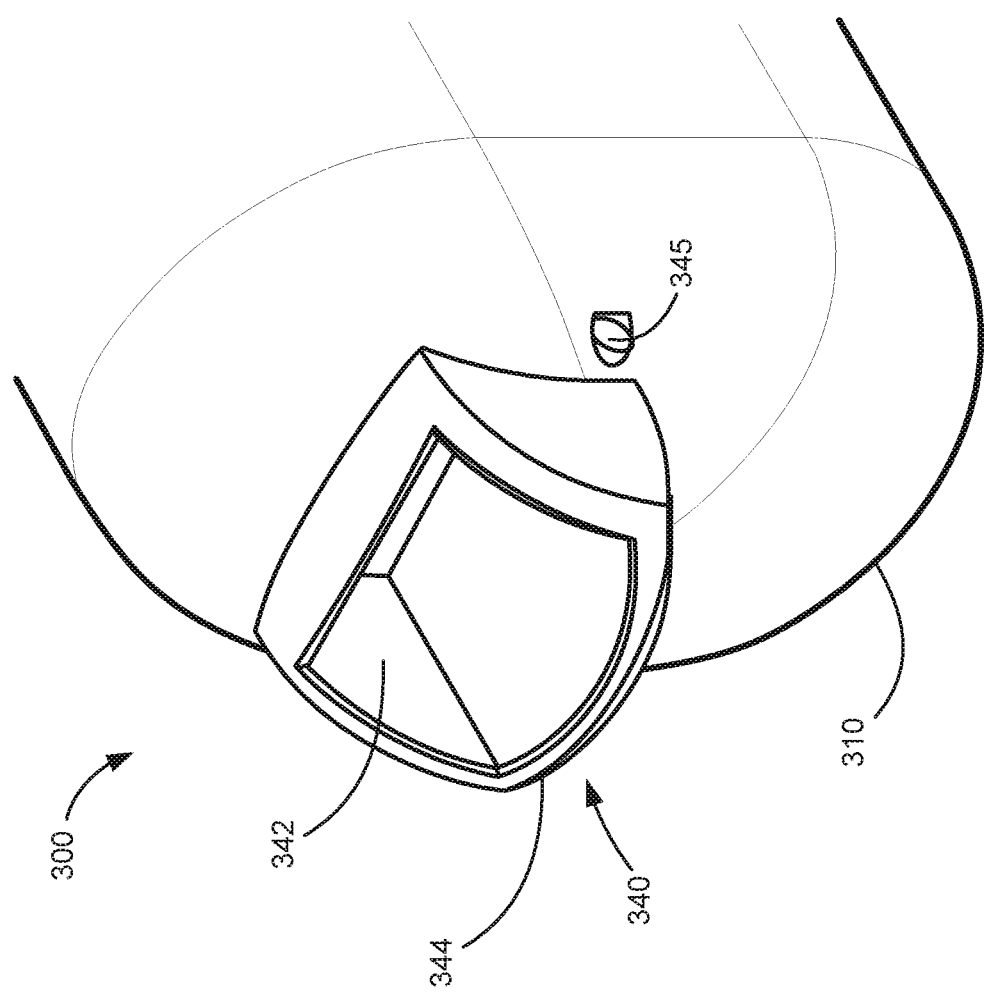
FIG. 3A is a front perspective view of a concealable mouthpiece in an active position.
Figure 3B:
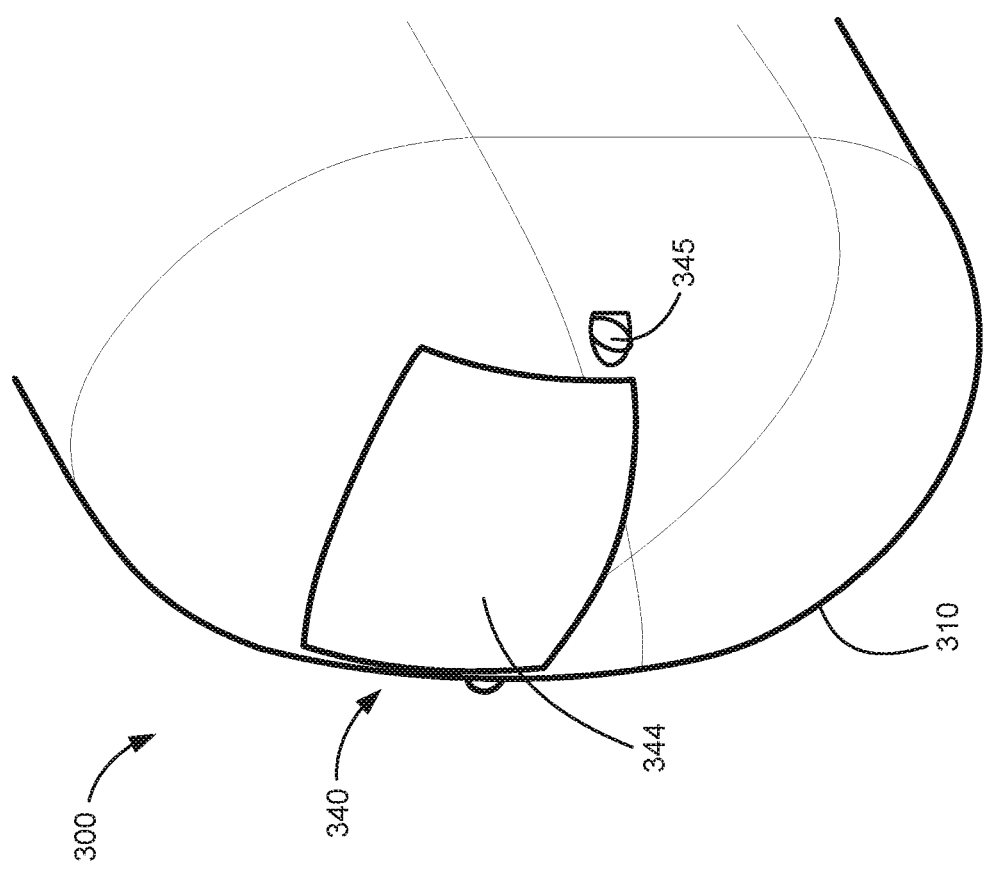
FIG. 3B is a front perspective view of the concealable mouthpiece shown in FIG. 3A in a stored position.
Figure 3D:
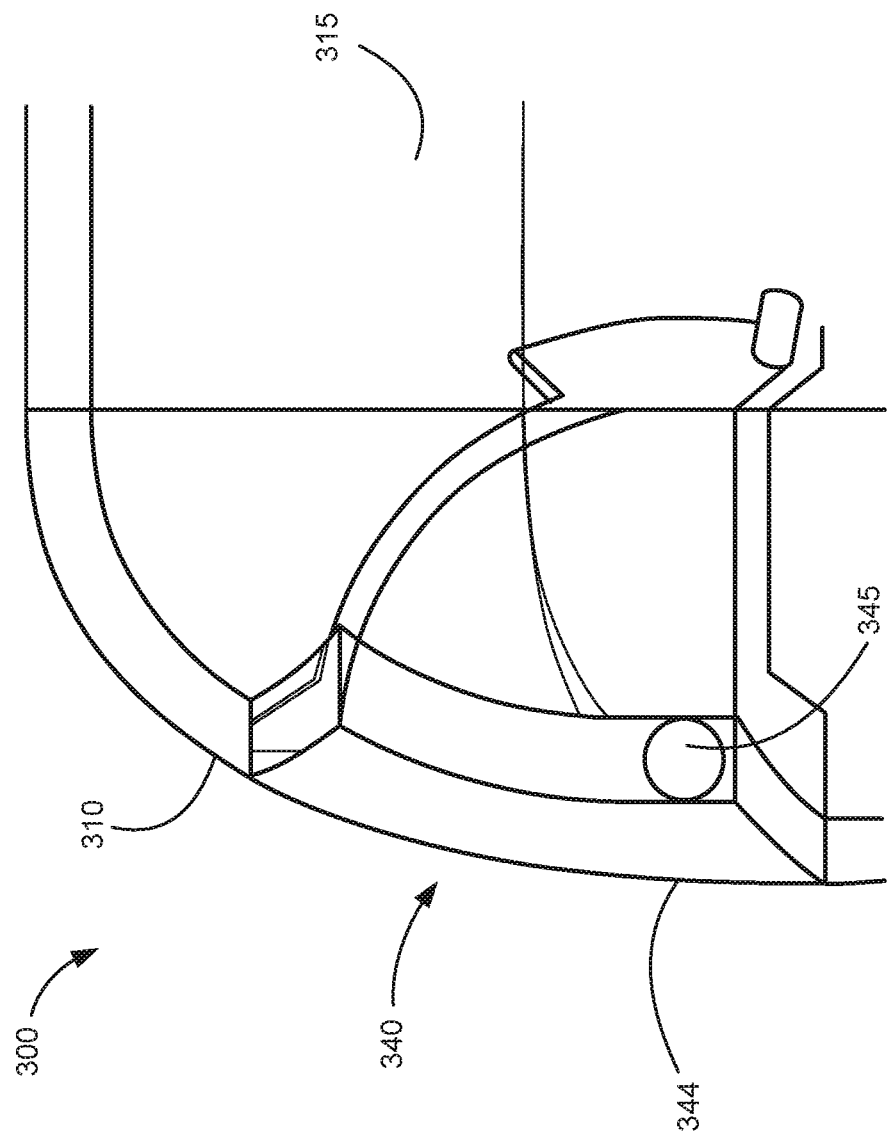
FIG. 3D is a cross-section view of the concealable mouthpiece shown in FIG. 3A in a stored position.

The retaining device 120 may allow the user to move the inhaler 150 into a predetermined stored position, shown in FIG. 1E, and a predetermined active position, shown in FIGS. 1B-1D, for example, by rotating the inhaler 150 and the retaining device 120. The inhaler 150 may remain coupled to the retaining device 120, and the retaining device 120 may remain coupled to the spacer housing 110 during transition between the stored position and the active position. In the stored position, the inhaler 150 may be completely contained in the spacer housing 110. The inhaler 150 may occupy the spacer chamber 115, which may allow the spacer 100 and inhaler 150 to be more compact than they would be if they were separated and/or the inhaler 150 did not occupy the spacer chamber 115 when in the stored position. The inhaler mouthpiece 151 may be aimed directly at the spacer housing 110 with little or no gap between them. Thus, the inhaler 150 may not be able to effectively deliver medication to the user in the stored position.

In the active position, the inhaler 150 may be positioned to effectively deliver medication to the spacer chamber 115 and the user. The inhaler mouthpiece 151 may be aimed into the spacer chamber 115 and have sufficient distance between the inhaler mouthpiece 151 and the portion of the spacer housing 110 at which the mouthpiece is aimed for the medication to slow and disperse in the spacer chamber 115. The inhaler 150 may protrude from the spacer housing 110 in the active position, which may provide access to the inhaler 150 by the user. The user may be able to depress the canister 154 to release medication into the spacer chamber. Because the inhaler 150 protrudes from the spacer housing 110, the amount of usable space in the spacer housing 110 may be increased when the inhaler 150 is in the active position. As a result, the spacer housing 110 can be more compact while still effectively slowing the medication for inhalation by the user. In some embodiments, the spacer housing 110 may be telescoping to allow the user to further increase the usable space.

The spacer housing 110 may include a cover 130. The cover 130 may be rotatably coupled to the spacer housing 110 (e.g., by a hinge 132), which may allow the cover 130 to be opened without decoupling from the spacer housing 110. The cover 130 may rotate in any direction, such as vertically, horizontally, and/or the like. The cover 130 may include a sliding door 135 that can be adjusted to increase or decrease the length of the cover 130. In a closed position with the sliding door 135 extended, the cover 130 may completely conceal the inhaler 150 and the spacer chamber 115. The inhaler 150 may need to be in the stored position for the cover 130 to close completely with the sliding door 135 extended. In some embodiments, a locking mechanism (not shown), such as a latch, hook, clip, ridge and channel, nub and dimple, magnet, friction coupling, and/or the like, may secure the cover 130 in the closed position. The cover 130 may automatically move to the open position when the locking mechanism is released (e.g., a spring element may rotate the cover 130 to the open position).

The cover 130 may be opened to provide access to the inhaler 150 and allow the user to change the inhaler 150 from the stored position to the active position or vice versa. The cover 130 may be closed with the sliding door 135 fully retracted or partially extended when the inhaler 150 is in the active position. The sliding door 135 may be unable to extend completely to a closed position when the inhaler 150 is in the active position but may frictionally engage the inhaler 150 to provide additional stability. Accordingly, the user may have easy access the top of the inhaler 150 for actuating the inhaler 150. Alternatively, or in addition, a plug or flexible material (not shown) may cover the top of the inhaler 150 but still allow the user to actuate the inhaler 150. The plug or flexible material may be made of silicone, rubber, polymer, and/or the like.

The cover 130 may substantially seal the spacer chamber 115 when the cover 130 is closed and the inhaler 150 is in the active position. Much of the air exchange between the spacer chamber 115 and the outside may occur due to holes in the inhaler 150 between the canister 154 and the inhaler actuator/housing 152. Accordingly, the advantages of completely sealing the spacer chamber 115 may be minimal. The spacer chamber 115 may be substantially sealed if the area of any gaps in the spacer housing 110, not including the mouthpiece 140 and any intake valves (not shown), is no more than 0.5, 1, 2, 3, 4, 5, 10, etc. times larger than the area of the holes in the inhaler 150. The cover 130 may touch the inhaler 150 when the cover 130 is closed and the inhaler 150 is in the active position, but the cover 130 may not be shaped to conform to the inhaler 150. In another embodiment, the cover 130 may be shaped to conform to the inhaler 150 when the inhaler 150 is in the active position.

The spacer housing 110 may include an air intake valve (not shown) in addition to and/or instead of gaps in the spacer housing 110. The air intake valve may include a one-way valve (not shown) configured to let air into the spacer chamber 115 but not out. Insufficient medication may reach the lower airway target if the user inhales too quickly, so the intake valve may alert the user if the user's inhalation rate is above a predetermined threshold. For example, the intake valve may be configured to make a high-pitch whistling sound above the predetermined threshold, and/or an electronic switch may be triggered, which may light an indicator and/or produce a noise using a speaker. The predetermined threshold may be between 25 and 30 liters per minute in some embodiments.

The spacer housing 110 may include a mouthpiece 140 that allows the user to inhale the medication contained in the spacer chamber 115. The mouthpiece 140 may be configured to switch between an active position in which the medication can be retrieved from the spacer chamber 115 and a stored position in which the mouthpiece 140 is concealed. In an embodiment, the mouthpiece 140 may include a flap (not shown) that rotates between an open position that provides an opening 142 to the spacer chamber 115 through which medication can be inhaled and a closed position that covers the opening 142. A locking mechanism (not shown), such as a latch, hook, clip, ridge and channel, nub and dimple, magnet, friction coupling, and/or the like, may secure the flap in the closed position. A spring, gravity, and/or the like may automatically rotate the flap to the active position when the locking mechanism is released. Alternatively, or in addition, the mouthpiece 140 may rotate to hide the opening 142, the mouthpiece 140 may be telescoping, the mouthpiece 140 may slide on a track (not shown), the opening 142 may be covered by a sliding door (not shown), the mouthpiece 140 may be made of a flexible material and may invert into the spacer chamber 115, the mouthpiece 140 may be covered by a cap (not shown), and/or the like to switch between the active and stored positions. The mouthpiece 140 may not protrude from the spacer housing 110 while in the stored position, and/or the cap may be flush with the spacer housing 110 in some embodiments.

The mouthpiece 140 may include one or more exhaust ports (not shown) and/or a one-way valve (not shown) coupled to the spacer chamber 115 to prevent the user from exhaling into the spacer chamber 115, which may dispel the medication from the spacer chamber 115. The exhaust ports may be positioned so the user's lips do not cover the exhaust ports. The exhaust ports may each include a one-way exhaust valve (not shown) that prevent medication from escaping during inhalation. The one-way valve coupled to the spacer chamber 115 may allow air and medication from the spacer chamber 115 to travel out the mouthpiece 140 but may prevent air from entering the spacer chamber 115 through the mouthpiece 140. The one-way valve may include a duckbill valve, a flat valve supported by ribbing that may include any number of sections or no sections, and/or the like.

In an embodiment, the retaining device 120 may be configured to receive an inhaler 150 that includes a canister 154 and an inhaler actuator/housing 152. The retaining device 120 may secure the inhaler actuator/housing 152 in a desired position, and the inhaler actuator/housing 152 may secure the canister 154. Alternatively, or in addition, the retaining device 120 may be configured to receive an inhaler including a canister 154 but without an inhaler actuator/housing 152. For example, the retaining device 120 may include a nozzle block (not shown) and/or a nozzle (not shown) configured to disperse medication from the canister 154 into the spacer chamber 115. To secure the canister 154, the restraining band 124 may be configured to encircle the canister 154, and/or the nozzle block may provide sufficient friction to hold the canister 154. The spacer 100 may include a dose-counting mechanism (not shown) that is visible to the user (e.g., through a window, gap, or the like) so the number of doses used and/or remaining can be seen by the user.

FIGS. 2A-2E are perspective and cross-section views of another embodiment of a spacer 200 configured to store an inhaler 250. The spacer 200 may include a spacer housing 210 that defines a spacer chamber 215 for receiving medication discharged by the inhaler 250. The spacer chamber 215 may include an elongated longitudinal axis and a cross-section normal to the longitudinal axis that is oval shaped, a hybrid between a rectangle and an ellipse, and/or the like. As with the first spacer 100 shown in FIGS. 1A-1E, the length, width, and/or height of the second spacer 200, shown in FIGS. 2A-2E, may be selected based on dimensions of a selected pants pocket, dimensions of the inhaler 250, the space needed to slow the medication, and/or the like so that the spacer 200 fits in the selected pants pocket, can completely store the inhaler, and can effectively deliver medication to a lower airway target. The inhaler 250 may include a canister 254 and an inhaler actuator/housing 252, or the inhaler 250 may include a canister 254 only.

The spacer 200 may include an inhaler container 220 to which the inhaler 250 may be removeably coupled. The inhaler container 220 may frictionally engage with the inhaler 250 to secure the inhaler 250. For example, the inhaler container 220 may include a cuff 224 into which the inhaler mouthpiece 251 may be inserted. The user may need to apply a force greater than a predetermined threshold (e.g., gravity, a predetermined multiple of gravity, etc.) to remove the inhaler mouthpiece 251 from the cuff 224. Otherwise, the inhaler 250 may not move and/or may move minimally relative to the inhaler container 220. A base 228 and an upper sealing member 226 may further support and constrain movement of the inhaler 250.

The inhaler container 220 may include one or more nubs 222 configured to move along corresponding tracks 221 in the spacer housing 210. In an embodiment, the inhaler container 220 may include two nubs 222 on opposite sides of the inhaler container 220, and the spacer housing 210 may include corresponding tracks on opposite sides of the spacer housing 210 (e.g., parallel tracks in a plane normal to the vertical axis). The user may slide the nubs 222 along the tracks 221 to transition the inhaler container 220 and the inhaler 250 from the stored position, shown in FIG. 2C, to the active position, shown in FIGS. 2A, 2B, and 2E. In the stored position, the inhaler 250 may be completely contained in the spacer housing 210, and the inhaler mouthpiece 251 may be aimed directly at the spacer housing 210 with little or no gap between them. In the active position, the inhaler 250 may be pointed at or substantially at the mouth piece 240 with sufficient distance between the inhaler mouthpiece 251 and the portion of the spacer housing 210 at which the inhaler mouthpiece 251 is aimed for the medication to slow and disperse in the spacer chamber 215. The inhaler 250 may remain secured by the inhaler container 220, and the inhaler container 220 may remain coupled to the inhaler housing 210 during transition between the stored position and the active position.

The tracks 221 may constrain the movement of the inhaler container 220 and the inhaler 250 so the stored position and the active position are consistent between uses. For example, the tracks 221 may terminate at the appropriate locations for each position. The inhaler container 220 and the inhaler 250 may also need to be rotated to transition from the stored position to the active position, so the nubs 222 may be able to rotate relative to the track 221. For example, to change the inhaler 250 from the stored to the active position, the user may slide the nubs 222 to the end of the track 221 and then rotate the inhaler container 220 and the inhaler 250. The track 221 may end and/or include stops (not shown) to prevent excessive movement of the inhaler controller 220. In some embodiments, the spacer housing 210 may include a rotation inducing mechanism (not shown), such as a hook configured to interface with a rod on the inhaler container 220 or the inhaler actuator/housing 252 or vice versa, a ball configured to interface with a socket on the inhaler container 220 or the inhaler actuator/housing 252 or vice versa, and/or the like. Alternatively, or in addition, the tracks 221 may hook at the end to induce rotation. In an embodiment, the inhaler container 220 may include tracks (not shown) and the spacer housing 210 may include nubs (not shown). Alternatively, or in addition, the inhaler 250 may be secured in the spacer housing 210 by friction without the tracks 221 or nubs 222.

Once the inhaler container 220 and inhaler 250 have been shifted to the active position, the spacer chamber 215 may be completely sealed and/or almost completely sealed other than the mouthpiece 240, any intake valves (not shown), and holes in the inhaler 250. The inhaler container 220 may include an upper sealing member 226 and a lower sealing member 227 that seal the back of the spacer chamber 215. The upper and lower sealing members 226, 227 may be shaped like the spacer housing 210 to block the back of the spacer housing 210. The spacer housing 210, the upper sealing member 226, and/or the lower sealing member 227 may include a stabilizing and/or locking mechanism (not shown), such as a latch, hook, clip, ridge and channel, nub and dimple, magnet, friction coupling, and/or the like, configured to secure the inhaler container 220 and the inhaler 250 in the active position and/or the stored position. In some embodiments, the lower sealing member 227 and/or the upper sealing member 226 may include an intake valve (not shown) and/or one or more holes (not shown) to improve air flow when the user inhales.

The spacer housing 210 may be rotatably coupled to a cover 230, for example, by a pivot 232. The cover 230 may be configured to completely conceal the inhaler 250 when the cover 230 is in a closed position and the inhaler 250 is in the stored position. The cover 230 may be rotated by the user to an open position to provide access to the inhaler container 220 and the inhaler 250 so that the user can manipulate the inhaler container 220 and the inhaler 250 from the stored position to the active position. A locking mechanism (not shown), such as a latch, hook, clip, ridge and channel, nub and dimple, magnet, friction coupling, and/or the like, may be configured to secure the cover 230 in the open position and/or the closed position. Alternatively, or in addition, the cover 230 may be coupled to the spacer housing 210 by a hinge (not shown); the spacer housing 210 may be configured to break apart into two parts that pivot relative to each other (e.g., at a hinge); the cover 230 may retractably slide on a track system (not shown) to open and closed positions; the inhaler container 220 may include a top portion (not shown) that seals the spacer chamber 115 when the inhaler container 220 is in the stored position; and/or the like. In some embodiments, the cover 230 may not be continuous so the cover 230 can clear the spacer housing 210

Either embodiment may include one or more ergonomic features to improve handling of the device. For example, the spacer 100, 200 may include a traction element (not shown), such as finger grooves, finger grips, a grip pad on the bottom of the spacer housing 110, 120 and/or inhaler 150, 250, and/or the like, which may be made using over molded rubber, silicon, and/or the like. The traction element may improve the user's grasp on and/or the stability of the spacer 100, 200, for example, when the user is actuating the inhaler 150, 250. A carabiner hole and/or key-ring hole (not shown) may allow the user to secure the spacer 100, 200 to their person and improve portability. A sleeve (not shown), such as a silicon wrap, may slide over the device to protect the spacer 100, 200, personalize the spacer 100, 200, provide traction, provide a hole for a carabiner and/or key ring, and/or the like.

In some embodiments, the spacer 100, 200 may include and/or be configured to receive a system to wirelessly transmit data on use of the spacer 100, 200. For example, the system may include a GPS component configured to record the day, time, location, etc. of each actuation. The system may transmit the recorded information to a smartphone app., doctor's office, server, etc. manually and/or automatically using a wired and/or wireless communication device (e.g., Bluetooth). Alternatively, or in addition, the system may transmit an indication of the actuation to a smartphone app., and the smartphone may record the day, time, location, etc. of the actuation.

FIGS. 3A-3D are perspective and cross-section views of a concealable mouthpiece 340 on a spacer 300. A user may be able to transition the mouthpiece 340 between an active position, shown in FIGS. 3A and 3C, and a stored position, shown in FIGS. 3B and 3D. In the active position, the mouthpiece 340 may allow the user to inhale medication from a spacer chamber 315 through a mouthpiece opening 342. In the stored position, the mouthpiece 340 may completely or substantially seal the spacer chamber 315 so medication in the spacer chamber 315 cannot exit through the mouthpiece 340. In the stored position, the mouthpiece 340 may also be configured to be flush with the spacer housing 310, which may improve portability and/or storage of the spacer 300 when not in use.

The mouthpiece 340 may include a door 344 configured to rotate about a pivot point to switch between the active and stored positions. The pivot point may be coincident with a pin 345 to which the door 344 is rotatably coupled. The user may rotate the door 344 between the active and stored positions to expose or conceal the mouthpiece opening 342. In some embodiments, the mouthpiece 340 may be spring loaded and/or gravitationally loaded, and the user may push the door 344 and/or a button to release the mouthpiece 340 from the stored position. Alternatively, or in addition, the mouthpiece 340 may include a tab (not shown) to allow the user to shift the mouthpiece 340 between the active and stored positions.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the scope of the disclosure. For example, any combination of features from the first and second spacer embodiments 100, 200 may be used to create a spacer according to this disclosure. The scope of the present disclosure should, therefore, be determined only by the following claims.

The invention claimed is:

1. A spacer apparatus to slow the delivery of medication released from an inhaler, the spacer apparatus comprising:
    a spacer housing defining a spacer chamber, wherein the spacer chamber is elongated along a longitudinal axis such that a volume of the spacer chamber provides space to slow medication discharged by the inhaler to effectively deliver the medication to lungs of a user;
    a mouthpiece to facilitate inhalation of the medication contained in the spacer chamber;
    a retaining device coupled to the spacer housing and configured to receive the inhaler; and
    a communication system to transmit data on the use of the spacer, wherein the spacer housing is configured to receive the communication system.

2. The spacer apparatus of claim 1, wherein the retaining device is configured to shift the inhaler from a stored position to an active position in which the inhaler is able to deliver the medication to the spacer chamber.

3. The spacer apparatus of claim 1, wherein in the closed position the inhaler is completely contained in the spacer housing.

4. The spacer apparatus of claim 1, wherein the data on the use of the spacer indicates an actuation of the inhaler.

5. The spacer apparatus of claim 1, wherein the communication system is configured to transmit the data on the use of the spacer to at least one of a smartphone, a doctor's office, and a server.

6. The spacer apparatus of claim 1, further comprising a global positioning system (GPS) component configured to record at least a day, time, and location of each actuation of the inhaler.

7. The spacer apparatus of claim 1, wherein the communication system is further configured transmit the data on the use of the spacer to a smartphone application configured to record at least a day, time, and location of an actuation of the inhaler.

8. The spacer apparatus of claim 1, wherein the communication system comprises a wired and/or wireless communication device.

9. The spacer apparatus of claim 1, wherein the spacer housing comprises a cover configured to provide user access to the inhaler, and wherein the spacer housing is configured to completely conceal the inhaler when the cover is in a closed position.

10. The spacer apparatus of claim 1, wherein the retaining device is rotatably coupled to the spacer housing and rotates about a pivot point, wherein the pivot point is located in the spacer housing, and wherein the pivot point is configured to move relative to the spacer housing.

11. The spacer apparatus of claim 1, wherein the retaining device is configured to receive a canister containing pressurized medication or an inhaler actuator configured to disperse released medication and house the canister.

12. The spacer apparatus of claim 1, further comprising an intake element configured to alert the user if the user's inhalation rate is above a predetermined threshold.

13. The spacer of apparatus of claim 1, further comprising an electronic switch configured to be triggered if the user's inhalation rate is above a predetermined threshold.

14. The spacer of apparatus of claim 13, wherein the electronic switch is configured to light an indicator.

15. The spacer of apparatus of claim 13 or 14, wherein the electronic switch is configured to produce a noise using a speaker.

16. A method to track usage of a delivery system for an inhalable, the method comprising:
    detecting a delivery of an inhalable by an inhaler through a spacer, the spacer comprising a spacer chamber and coupled to a mouthpiece, wherein the spacer chamber is elongated along a longitudinal axis such that a volume of the spacer chamber provides space to slow medication discharged by the inhaler to effectively deliver the medication to lungs of a user;
    recording usage data related to the delivery, wherein the usage data comprises an actuation of an inhaler; and
    transmitting the usage data via a communication system of the spacer.

17. The method of 16, wherein the usage data comprises a day, time, and location of each actuation of the inhaler.

18. The method of 16, wherein transmitting the usage data comprises transmitting the usage data to at least one of a smartphone, a doctor's office, and a server 20, the method of 16, wherein transmitting the usage data comprises transmitting the usage data to a smartphone application configured to record at least a day, time, and location of an actuation of the inhaler.

19. The method of 16, further comprising alerting a user if the user's inhalation rate is above a predetermined threshold.

20. The method of 19, wherein alerting the user comprises illuminating an indicator light.

21. The method of 19, wherein alerting the user comprises producing a noise using a speaker.

* * * * *